United States Patent
Iimura et al.

(10) Patent No.: US 6,706,741 B2
(45) Date of Patent: Mar. 16, 2004

(54) ACETYLCHOLINESTERASE INHIBITORS CONTAINING 1-BENZYL-PYRIDINIUM SALTS

(75) Inventors: Yoichi Iimura, Ibaraki (JP); Takashi Kosasa, Ibaraki (JP)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 10/221,963

(22) PCT Filed: Apr. 9, 2001

(86) PCT No.: PCT/JP01/03046

§ 371 (c)(1), (2), (4) Date: Sep. 18, 2002

(87) PCT Pub. No.: WO01/78728

PCT Pub. Date: Oct. 25, 2001

(65) Prior Publication Data

US 2003/0069289 A1 Apr. 10, 2003

(30) Foreign Application Priority Data

Apr. 13, 2000 (JP) .......................... 2000-112627

(51) Int. Cl.[7] ...................... A61K 31/44; C07D 211/70; C07D 211/82
(52) U.S. Cl. .................. 514/358; 546/340; 546/343
(58) Field of Search ................ 546/343, 340; 514/358

(56) References Cited

U.S. PATENT DOCUMENTS

| 4,895,841 | A |   | 1/1990 | Sugimoto et al. |         |
|-----------|---|---|--------|-----------------|---------|
| 5,606,064 | A |   | 2/1997 | Lensky          |         |
| 6,252,081 | B1| * | 6/2001 | Iimura          | 546/206 |

FOREIGN PATENT DOCUMENTS

| EP | 535496   | A1 |   | 4/1993 |
|----|----------|----|---|--------|
| EP | 0 711 756|    | * | 7/1999 |
| JP | 8-225527 | A  |   | 9/1996 |
| JP | 11-263774| A  |   | 9/1999 |
| WO | 99/36405 |    | * | 7/1999 |

* cited by examiner

Primary Examiner—D. Margaret Seaman
(74) Attorney, Agent, or Firm—Birch, Stewart, Kolasch & Birch, LLP

(57) ABSTRACT

The present invention provides an excellent acetylcholinesterase inhibitor. That is, it provides an acetylcholinesterase inhibitor comprising a 1-benzylpyridinium salt represented by the following formula:

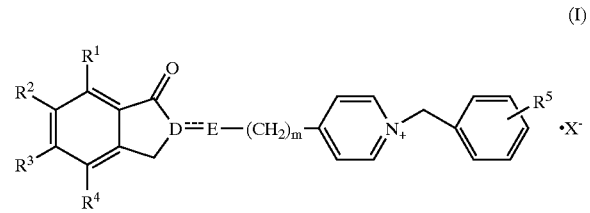

(I)

wherein $R^1$, $R^2$, $R^3$ and $R^4$ are the same as or different from each other and each represents a hydrogen atom, a halogen atom, a hydroxyl group, a nitrile group, a $C_{1-6}$ alkyl group, a $C_{1-6}$ alkoxy group etc.; $R^5$ represents a hydrogen atom, a halogen atom etc.; the partial structure:

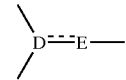

is a group represented by the formula $>C(R^6)—CH_2—$ (wherein $R^6$ is a hydrogen atom or a halogen atom) or $>C=CH—$; X– represents a halide ion or organic sulfonic acid ion; and m is 0 or an integer from 1 to 5.

15 Claims, No Drawings

ACETYLCHOLINESTERASE INHIBITORS CONTAINING 1-BENZYL-PYRIDINIUM SALTS

This application is the national phase under 35 U.S.C. §371 of PCT International Application No. PCT/JP01/03046 which has an International filing date of Apr. 9, 2001, which designated the United States of America.

TECHNICAL FIELD

The present invention relates to a novel acetylcholinesterase inhibitor.

PRIOR ART

Usefulness of an acetylcholinesterase inhibitor as an agent for treating and improving senile dementia such as Alzheimer type senile dementia, or cerebrovascular dementia, attention deficit hyperactivity disorder etc. came to be clinically highly regarded. In particular, donepezil hydrochloride (1-benzyl-4-[(5,6-dimethoxy-1-indanone)-2-yl]methylpiperidine hydrochloride) found with efforts of the present inventors is the only acetylcholinesterase inhibitor at present which can be sufficiently useful in respect of pharmacological activity, side effects, administration frequency, administration form etc., and fulfilling hopes of many patients and their families in nursing and clinical fields. In addition to donepezil hydrochloride, there are known acetylcholinesterase inhibitors such as rivastigmine (3-[1-(dimethylamino)ethyl]phenyl N-ethyl-N-methylcarbamate), metrifonate (dimethyl 2,2,2-trichloro-1-hydroxyethyl) phosphate), tacrine hydrochloride (1,2,3,4-tetrahydro-9-acridinamine), galanthamine hydrobromide, neostigmine, physostigmine etc. On one hand, there are some reports on processes for producing donepezil derivatives including donepezil hydrochloride, and for example JP-A 8-225527 and JP-A 11-263774 disclose a process for producing benzylpiperidylmethyl indanones, characterized by hydrogenating pyridinium salts with hydrogen in the presence of a hydrogenating catalyst.

It has been desired to provide highly useful acetylcholinesterase inhibitors in addition to donepezil hydrochloride.

DISCLOSURE OF THE INVENTION

In view of the circumstances described above, the present inventors made extensive study through which they found that both a compound represented by the formula:

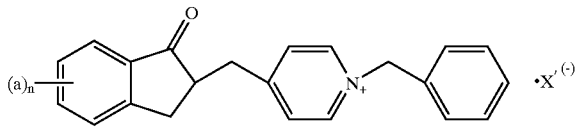

(wherein the "a" moieties are the same as or different from each other and each represents a hydrogen atom or a $C_{1-6}$ alkoxy group; n is an integer from 1 to 4; and $X'^{(-)}$ represents a halide ion) and a compound represented by the formula:

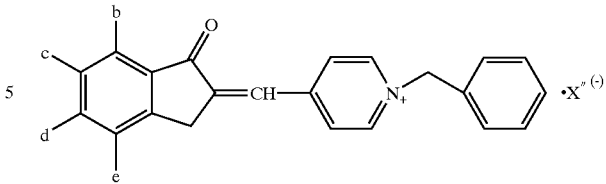

(wherein b, c, d and e are the same as or different from each other and each represents a hydrogen or a linear or branched $C_{1-6}$ alkyl, $C_{1-6}$alkoxy, $C_{1-6}$alkoxy carbonyl, $C_{1-6}$alkyl aminocarbonyloxy, di ($C_{1-6}$alkyl)-aminocarbonyloxy or a halogen; and $X''^{(-)}$ represents an anion in the series of chloride, bromide, iodide and sulfate) exhibit an excellent inhibitory action on acetylcholinesterase. Further, on the basis of these findings, they found that a 1-benzylpyridinium salt represented by the formula:

(I)

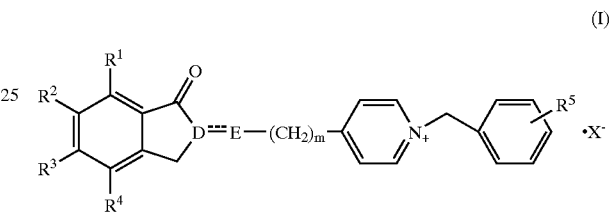

(wherein $R^1$, $R^2$, $R^3$ and $R^4$ are the same or different, and represent a hydrogen atom, a halogen atom, a hydroxyl group, a nitrile group, a $C_{1-6}$ alkyl group, a $C_{1-6}$ alkoxy group, a $C_{1-6}$alkoxy carbonyl group, a $C_{1-6}$ alkyl aminocarbonyloxy group or a di ($C_{1-6}$ alkyl)-aminocarbonyloxy group; $R^5$ represents a hydrogen atom, a halogen atom, a $C_{1-6}$alkyl group, a $C_{2-6}$ alkenyl group or a $C_{2-6}$ alkynyl group; the partial structure:

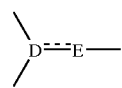

is a group represented by the formula >C($R^6$)—CH$_2$— (wherein $R^6$ is a hydrogen atom or a halogen atom) or >C=CH—; $X^-$ represents a halide ion or organic sulfonic acid ion; and m is 0 or an integer from 1 to 5) exhibits an excellent inhibitory action on acetylcholinesterase, and accomplished the present invention.

That is, the first aspect according to the present invention is (1) an acetylcholinesterase inhibitor comprising a 1-benzylpyridinium salt represented by the above formula (I). Further, (2) in the above item (1), $R^1$, $R^2$, $R^3$ and $R^4$ may be the same as or different from each other and each represents a hydrogen atom or a $C_{1-6}$ alkoxy group; (3) in the above item (1), $R^1$, $R^2$ $R^3$ and $R^4$ may be the same as or different from each other and each represents a hydrogen atom or a methoxy group; (4) in the above item (1), $R^1$ and $R^4$ may represent a hydrogen atom; and $R^2$ and $R^3$ may represent a methoxy group; (5) in the above item (1), $R^5$ may be a hydrogen atom; (6) in the above item (1), the partial structure:

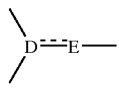

may be a group represented by the formula >C (R⁶) —CH₂— (wherein R⁶ is a hydrogen atom or a halogen atom); (7) in the above item (1), m may be 0, 2 or 4; (8) in the above item (1), the halide ion represented by X⁻ maybe a chloride ion, bromide ion or iodide ion, preferably a chloride ion or bromide ion; (9) in the above item (1), the organic sulfonic acid ion represented by X⁻ may be a methanesulfonate ion, trifluoromethanesulfonate ion, ethanesulfonate ion, benzenesulfonate ion, toluenesulfonate ion or camphor sulfonate ion; (10) in the above item (1), the 1-benzylpyridinium salt may be a compound represented by the formula:

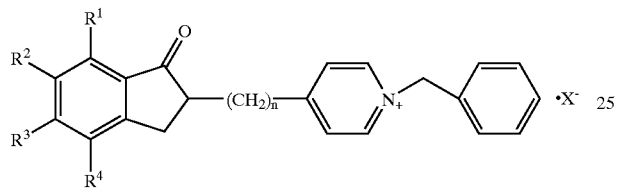

wherein $R^1$, $R^2$, $R^3$, $R^4$ and $X^-$ have the same meanings as defined above; and n is an integer from 1 to 6; (11) in the above item (1), the 1-benzylpyridinium salt may be a compound represented by the formula:

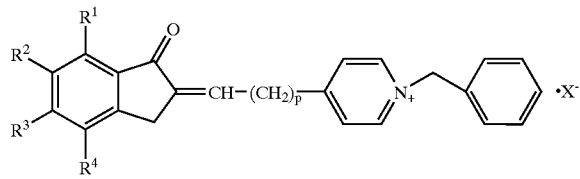

wherein $R^1$, $R^2$, $R^3$, $R^4$ and $X^-$ have the same meanings as defined above; and p is 0 or an integer from 1 to 5; (12) in the above item (1), the preparation may be an agent for treating, preventing or improving senile dementia, cerebrovascular dementia or attention deficit hyperactivity disorder; and (13) in the above item (12), the senile dementia may be Alzheimer type senile dementia.

The second aspect according to the present invention is (14) a pharmaceutical preparation comprising a 1-benzylpyridinium salt represented by the formula:

(I)

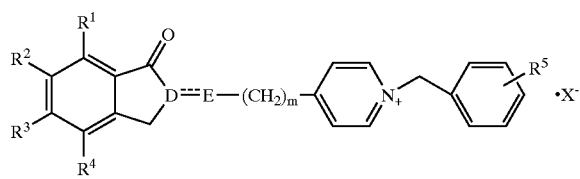

wherein $R^1$, $R^2$, $R^3$, $R^4$, $R^5$, the partial structure:

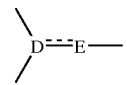

$X^-$ and m have the same meanings as defined above. Further, the third aspect according to the present invention is (15) use of a 1-benzylpyridinium salt represented by the formula:

(I)

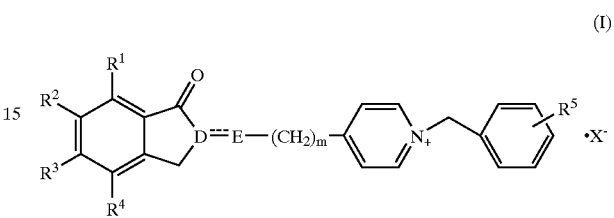

(wherein $R^1$, $R^2$, $R^3$, $R^4$, $R^5$, the partial structure:

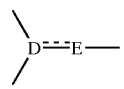

$X^-$ and m have the same meanings as defined above) for producing an acetylcholinesterase inhibitor.

The present invention provides a method of preventing, treating or improving a disease against which an inhibitory action on acetylcholinesterase is efficacious for prevention, treatment or improvement, by administering a pharmacologically effective dose of the 1-benzylpyridinium salt represented by the above formula (I) to a patient.

In the present invention, the disease against which an inhibitory action on acetylcholinesterase is efficacious for prevention, treatment or improvement includes senile dementia such as Alzheimer type senile dementia, and cerebrovascular dementia and attention deficit hyperactivity disorder.

Hereinafter, the meanings of symbols, terms etc. used in the specification are described, and the present invention is described in detail.

In the specification, the structural formulae of the compound may, for convenience' sake, indicate a certain isomer, but the present invention encompasses all possible isomers which can occur in the structures of the compound, for example geometric isomer, optical isomer based on asymmetrical carbon, stereoisomer and tautomer, and a mixture of such isomers, so the compound according to the present invention may be any isomers or a mixture thereof without limitation to the formulae shown for convenience' sake. Accordingly, the compound according to the present invention can have an intramolecular asymmetrical carbon, thus occurring as optically active isomers or racemic modifications, and any of such compounds are included in the present invention without limitation. When there is crystal polymorphism, the compound according to the present invention may be in a single crystal form or a mixed crystal form without limitation. Compound (I) or salts thereof may be anhydrides or hydrates, any of which fall under the claims in the specification. Further, metabolites formed by decomposition of Compound (I) in vivo, and prodrugs of Compound (I) or salts thereof, also fall under the claims in the specification.

The "halogen atom" used in the specification refers to an atom such as a fluorine atom, a chlorine atom, a bromine atom or an iodine atom, preferably a fluorine atom, a chlorine atom or a bromine atom.

The "$C_{1-6}$ alkyl group" represented by $R^1$, $R^2$, $R^3$ and $R^4$ in the specification refers to an alkyl group having 1 to 6 carbon atoms, and examples thereof include a methyl group, ethyl group, n-propyl group, iso-propyl group, n-butyl group, iso-butyl group, sec-butyl group, tert-butyl group, n-pentyl group, 1,1-dimethylpropyl group, 1,2-dimethylpropyl group, 2,2-dimethylpropyl group, 1-ethylpropyl group, 2-ethylpropyl group, n-hexyl group, 1-methyl-2-ethylpropyl group, 1-ethyl-2-methylpropyl group, 1,1,2-trimethylpropyl group, 1-propylpropyl group, 1-methylbutyl group, 2-methylbutyl group, 1,1-dimethylbutyl group, 1,2-dimethylbutyl group, 2,2-dimethylbutyl group, 1,3-dimethylbutyl group, 2,3-dimethylbutyl group, 2-ethylbutyl group, 2-methylpentyl group, 3-methylpentyl group etc., preferably a methyl group, ethyl group, n-propyl group, iso-propyl group, n-butyl group, iso-butyl group and tert-butyl group.

The "$C_{1-6}$ alkoxy group" represented by $R^1$, $R^2$, $R^3$ and $R^4$ in the specification refers to an alkoxy group having 1 to 6 carbon atoms, and examples thereof include a methoxy group, ethoxy group, n-propoxy group, iso-propoxy group, sec-propoxy group, n-butoxy group, iso-butoxy group, sec-butoxy group, tert-butoxy group, n-pentyloxy group, iso-pentyloxy group, sec-pentyloxy group, n-hexoxy group, iso-hexoxy group, 1,1-dimethylpropyloxy group, 1,2-dimethylpropoxy group, 2,2-dimethylpropyloxy group, 2-ethylpropoxy group, 1-methyl-2-ethylpropoxy group, 1-ethyl-2-methylpropoxy group, 1,1,2-trimethylpropoxy group, 1,1,2-trimethylpropoxy group, 1,1-dimethylbutoxy group, 1,2-dimethylbutoxy group, 2,2-dimethylbutoxy group, 2,3-dimethylbutyloxy group, 1,3-dimethylbutyloxy group, 2-ethylbutoxy group, 1,3-dimethylbutoxy group, 2-methylpentoxy group, 3-methylpentoxy group, hexyloxy group etc., preferably a methoxy group, ethoxy group, n-propoxy group and iso-propoxy group.

The "$C_{1-6}$ alkoxycarbonyl group" represented by $R^1$, $R^2$, $R^3$ and $R^4$ in the specification refers to a group in which a $C_{1-6}$ alkoxy group having the same meaning as defined above bound to a carbonyl group. For example, a methoxycarbonyl group, ethoxycarbonyl group, n-propoxycarbonyl group, iso-propoxycarbonyl group, n-butoxycarbonyl group, iso-butoxycarbonyl group, tert-butoxycarbonyl group, pentyloxycarbonyl group, hexyloxycarbonyl group etc., preferably a methoxycarbonyl group, ethoxycarbonyl group, n-propoxycarbonyl group and iso-propoxycarbonyl group.

The "$C_{1-6}$alkyl aminocarbonyloxy group" represented by $R^1$, $R^2$, $R^3$ and $R^4$ in the specification refers to an aminocarbonyloxy group whose nitrogen atom has been substituted with a $C_{1-6}$alkyl group having the same meaning as defined above, and examples thereof include a methylaminocarbonyloxy group, ethylaminocarbonyloxy group, n-propylaminocarbonyloxy group, iso-propylaminocarbonyloxy group, n-butylaminocarbonyloxy group, iso-butylaminocarbonyloxy group, tert-butylaminocarbonyloxy group, n-pentylaminocarbonyloxy group, iso-pentylaminocarbonyloxy group, neopentylaminocarbonyloxy group, hexylaminocarbonyloxy group, 1-methylpropylaminocarbonyloxy group, 1-methyl butyl aminocarbonyloxy group, 2-methylbutylaminocarbonyloxy group etc.

The "di ($C_{1-6}$ alkyl)-aminocarbonyloxy group" represented by $R^1$, $R^2$, $R^3$ and $R^4$ in the specification refers to an aminocarbonyloxy group whose nitrogen atom has been substituted with two $C_{1-6}$ alkyl groups, and examples thereof include a dimethylaminocarbonyloxy group, diethylaminocarbonyloxy group, di(n-propyl)-aminocarbonyloxy group, di-(iso-propyl)-aminocarbonyloxy group, di(n-butyl)-aminocarbonyloxy group, di(iso-butyl)-aminocarbonyloxy group, di-(tert-butyl)-aminocarbonyloxy group, di(n-pentyl)-aminocarbonyloxy group, di-(iso-pentyl)-aminocarbonyloxy group, di-(neopentyl)-aminocarbonyloxy group, di-(n-hexyl)-aminocarbonyloxy group, di-(1-methylpropyl)-aminocarbonyloxy group, di-(1-methylbutyl)-aminocarbonyloxy group, di-(2-methylbutyl)-aminocarbonyloxy group etc.

As the preferable mode of $R^1$, $R^2$, $R^3$ and $R^4$ in the specification, $R^1$, $R^2$, $R^3$ and $R^4$ are the same as or different from each other and each represents a hydrogen atom, a halogen atom, a hydroxyl group, a nitrile group, a $C_{1-6}$alkyl group or a $C_{1-6}$ alkoxy group; more preferably, they are the same as or different from each other and each represents a hydrogen atom, a halogen atom, a hydroxyl group, a nitrile group or a $C_{1-6}$alkoxy group; further preferably, they are the same as or different from each other and each represents a hydrogen atom or a $C_{1-6}$alkoxy group; and the most preferably, $R^1$ and $R^4$ represent a hydrogen atom while $R^2$ and $R^3$ are the same as or different from each other and each represents a $C_{1-6}$ alkoxy group (for example, a methoxy group, ethoxy group etc.).

The "halogen atom" and "$C_{1-6}$ alkyl group" represented by $R^5$ in the specification refer to a halogen atom and $C_{1-6}$alkyl group each having the same meaning as defined above.

The "$C_{2-6}$ alkenyl group" represented by $R^5$ in the specification refers to an alkenyl group having 2 to 6 carbon atoms, and examples thereof include linear or branched $C_{2-6}$ alkenyl groups such as a vinyl group, allyl group, 1-propenyl group, isopropenyl group, 1-buten-1-yl group, 1-buten-2-yl group, 1-buten-3-yl group, 2-buten-1-yl group and 2-buten-2-yl group, preferably a vinyl group, allyl group and isopropenyl group.

The "$C_{2-6}$ alkynyl group" represented by $R^5$ in the specification refers to an alkynyl group having 2 to 6 carbon atoms, and examples thereof include linear or branched $C_{2-6}$ alkynyl groups such as an ethynyl group, 1-propynyl group, 2-propynyl group, butynyl group, pentynyl group and hexynyl group.

Preferable examples of $R^5$ in the specification include a hydrogen atom and a halogen atom (for example, a fluorine atom, chlorine atom, bromine atom etc.).

The partial structure:

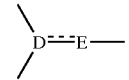

may be either a group represented by the formula $>C(R^6)$—$CH_2$— (wherein $R^6$ is a hydrogen atom or a halogen atom) or $>C=CH$—, preferably a group represented by the formula $>C(R^6)$—$CH_2$— wherein $R^6$ is a hydrogen atom or a halogen atom. Herein, the "halogen atom" represented by $R^6$ means an atom having the same meaning as the halogen atom in the above definition, and $R^6$ is preferably a hydrogen atom, fluorine atom, chlorine atom or bromine atom, more preferably a hydrogen atom or fluorine atom. That is, the group which can be represented by the partial structure is more preferably the formula $>CH$—$CH_2$—, $>C(F)$—$CH_2$—, $>C(Cl)$—$CH_2$— or $>C(Br)$—$CH_2$—, further preferably the formula $>CH$—$CH_2$— or $>C(F)$—$CH_2$—.

The "halide ion" represented by $X^-$ in the specification refers to a fluoride ion, chloride ion, bromide ion, iodide ion etc., preferably a chloride ion, bromide ion and iodide ion, more preferably a chloride ion and bromide ion, most preferably a chloride ion. The "organic sulfonic acid ion" represented by X⁻ refers to a methanesulfonate ion, trifluoromethanesulfonate ion, ethanesulfonate ion, benzenesulfonate ion, toluenesulfonate ion and camphor sulfonate ion etc.

In the specification, m is 0 or an integer from 1 to 5, whereupon the partial structure:

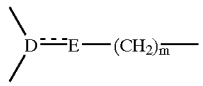

represents (1) the formula $>C(R^6)$—$CH_2$— or $>C$=$CH$— when m is 0, (2) the formula $>C(R^6)$—$(CH_2)_2$— or $>C$=$CH$—$(CH_2)$— when m is 1, (3) the formula $>C(R^6)$—$(CH_2)_3$— or $>C$=$CH$—$(CH_2)_2$— when m is 2, (4) the formula $>C(R^6)$—$(CH_2)_4$— or $>C$=$CH$—$(CH_2)_3$— when m is 3, (5) the formula $>C(R^6)$—$(CH_2)_5$— or $>C$=$CH$—$(CH_2)_4$— when m is 4, and (6) the formula $>C(R^6)$—$(CH_2)_6$— or $>C$=$CH$—$(CH_2)_5$— when m is 5, respectively (in the formula, $R^6$ has the same meaning as defined above). m is preferably 0, 2 or 4, more preferably 0 or 2.

The best mode of the acetylcholinesterase inhibitor in the present invention includes, for example, those acetylcholinesterase inhibitors comprising the following compounds. However, it goes without saying that the embodiments of the present invention are not limited to those acetylcholine esterase inhibitors comprising these compounds.

The acetylcholinesterase inhibitor comprises any one or two or more 1-benzylpyridinium salts selected from:
1-benzyl-4-(1-indanone-2-yl)methylpyridinium chloride;
1-benzyl-4-[(4-methoxy-1-indanone)-2-yl]methylpyridinium chloride;
1-benzyl-4-[(5-methoxy-1-indanone)-2-yl]methylpyridinium chloride;
1-benzyl-4-[(6-methoxy-1-indanone)-2-yl]methylpyridinium chloride;
1-benzyl-4-[(7-methoxy-1-indanone)-2-yl]methylpyridinium chloride;
1-benzyl-4-[(5,6-dimethoxy-1-indanone)-2-yl]methylpyridinium chloride;
1-benzyl-4-[(5,7-dimethoxy-1-indanone)-2-yl]methylpyridinium chloride;
1-benzyl-4-[(4,7-dimethoxy-1-indanone)-2-yl]methylpyridinium chloride;
1-benzyl-4-[(4,5-dimethoxy-1-indanone)-2-yl]methylpyridinium chloride;
1-benzyl-4-[(6,7-dimethoxy-1-indanone)-2-yl]methylpyridinium chloride;
1-benzyl-4-[(5,6,7-trimethoxy-1-indanone)-2-yl]methylpyridinium chloride;
1-benzyl-4-[(5,6-diethoxy-1-indanone)-2-yl]methylpyridinium chloride;
1-benzyl-4-(1-indanone-2-yl)methylpyridinium bromide;
1-benzyl-4-[(4-methoxy-1-indanone)-2-yl]methylpyridinium bromide;
1-benzyl-4-[(5-methoxy-1-indanone)-2-yl]methylpyridinium bromide;
1-benzyl-4-[(6-methoxy-1-indanone)-2-yl]methylpyridinium bromide;
1-benzyl-4-[(7-methoxy-1-indanone)-2-yl]methylpyridinium bromide;
1-benzyl-4-[(5,6-dimethoxy-1-indanone)-2-yl]methylpyridinium bromide;
1-benzyl-4-[(5,7-dimethoxy-1-indanone)-2-yl]methylpyridinium bromide;
1-benzyl-4-[(4,7-dimethoxy-1-indanone)-2-yl]methylpyridinium bromide;
1-benzyl-4-[(4,5-dimethoxy-1-indanone)-2-yl]methylpyridinium bromide;
1-benzyl-4-[(6,7-dimethoxy-1-indanone)-2-yl]methylpyridinium bromide;
1-benzyl-4-[(5,6,7-trimethoxy-1-indanone)-2-yl]methylpyridinium bromide; and
1-benzyl-4-[(5,6-diethoxy-1-indanone)-2-yl]methylpyridinium bromide.

The 1-benzylpyridinium salt represented by the above formula (I) as the active ingredient in the acetylcholinesterase inhibitor according to the present invention can be produced by a known method or its analogous method. Typical methods include a production method described, for example, in JP-A 11-263774 and a process for producing a benzylpyridinium salt (I) described in JP-A 8-225527.

The starting compound in production of the 1-benzylpyridinium salt (I) as the active ingredient in the acetylcholinesterase inhibitor according to the present invention may have formed a salt or a hydrate and is not particularly limited insofar as the reaction is not inhibited. Further, when Compound (I) according to the present invention is obtained in a free form, it can be converted in a usual manner into a salt which Compound (I) may form. Further, the resulting various isomers (for example, geometric isomer, optical isomer based on asymmetric carbon, stereoisomer, tautomer etc.) of Compound (I) according to the present invention can be purified and isolated by usual separating means, for example, re-crystallization, diastereomer salt method, enzyme fractionation method, and various kinds of chromatography (for example, thin layer chromatography, column chromatography, gas chromatography etc.).

The acetylcholinesterase preparation according to the present invention can be manufactured by a conventional method, and preferable preparation forms include tablets, powders, fine granules, granules, coated tablets, capsules, syrups, troches, inhalations, suppositories, injections, ointments, eye ointments, eye drops, nose drops, ear drops, poultices and lotions. Ordinarily used fillers, binders, disintegrating agents, lubricants, coloring agents, flavoring agents and as necessary stabilizers, emulsifiers, absorption promoters, surfactants, pH adjusters, preservatives and antioxidants can be used in pharmaceutical manufacturing, and ingredients used generally as starting materials for pharmaceutical preparations can be blended in a usual manner for manufacturing. These ingredients include e.g. (1) animal and vegetable oils such as soybean oil, tallow and synthetic glyceride; (2) hydrocarbons such as liquid paraffin, squalane and solid paraffin; (3) ester oils such as octyldodecyl myristate and isopropyl myristate; (4) higher alcohols such as cetostearyl alcohol and behenyl alcohol; (5) silicon resin; (6) siliconoil; (7) surfactants such as polyoxyethylene fatty ester, sorbitan fatty ester, glycerin fatty ester, polyoxyethylene sorbitan fatty ester, polyoxyethylene hardened castor oil and polyoxyethylene polyoxypropylene block copolymer; (8) water-soluble polymers such as hydroethyl cellulose, polyacrylic acid, carboxyvinyl polymer, polyethylene glycol, polyvinyl pyrrolidone and methyl cellulose; (9) lower alcohols such as ethanol and isopropanol; (10) polyvalent alcohols such as glycerin, propylene glycol, dipropylene glycol and sorbitol; (11) sugars such as glucose and sucrose; (12) inorganic powder such as silicic anhydride, aluminum magnesium silicate and aluminum silicate; and (13) pure water.

1) The fillers include e.g. lactose, corn starch, sucrose, glucose, mannitol, sorbitol, crystalline cellulose, silicon dioxide etc.; 2) the binders include e.g. polyvinyl alcohol, polyvinyl ether, methyl cellulose, ethyl cellulose, arabic gum, tragacanth, gelatin, shellac, hydroxypropyl cellulose, hydroxypropylmethyl cellulose, polyvinyl pyrrolidone, polypropylene glycol-polyoxyethylene block polymer, meglumine, calcium citrate, dextrin, pectin etc.; 3) the disintegrating agents include e.g. starch, agar, gelatin powder, crystalline cellulose, calcium carbonate, sodium bicarbonate, calcium citrate, dextrin, pectin, carboxymethyl cellulose calcium etc.; 4) the lubricants include e.g. magnesium stearate, talc, polyethylene glycol, silica, hardened vegetable oil etc.; 5) the coloring agents include e.g. those which are approved to be added to pharmaceutical preparations; 6) the flavoring agents include cocoa powder, menthol, aromatic powder, peppermint oil, borneol, cinnamon powder etc.; and 7) the antioxidants include those which are approved to be added to pharmaceutical preparations such as ascorbic acid and α-tocopherol.

1) The oral preparation is produced by mixing Compound (I) or a salt thereof with fillers and if necessary with a binder, a disintegrating agent, a lubricant, a coloring agent, flavoring agents etc.; and then forming it in a usual manner into powders, fine granules, granules, tablets, coated tablets, capsules etc. 2) The tablets and granules may be coated with a sugar or gelatin coating or if necessary with another suitable coating. 3) The liquid preparations such as syrups, injections, eye drops etc. are prepared by mixing with a pH adjuster, a solubilizer and an isotonizing agent together with, if necessary, a solubilizing aid, a stabilizer, a buffer, a suspension agent and an antioxidant, followed by forming it into the preparations in a usual manner. The liquid preparation may be formed into a freeze-dried product and the injection can be administered intravenously, subcutaneously or intramuscularly. Preferable examples of the suspension agent include methyl cellulose, Polysorbate 80, hydroxyethyl cellulose, arabic gum, tragacanth powder, sodium carboxymethyl cellulose, polyoxyethylene sorbitan monolaurate etc.; preferable examples of the solubilizing aid include polyoxyethylene hardened castor oil, Polysorbate 80, nicotinamide, polyoxyethylene sorbitan monolaurate etc.; preferable examples of the stabilizer include sodium sulfite, sodium metasulfite, ether etc.: preferable examples of the preservative include methyl p-oxybenzoate, ethyl p-oxybenzoate, sorbic acid, phenol, cresol, chlorocresol etc. 4) The agent for external application can be produced in any of the conventional processes without any limit to the process thereof. The starting base material can make use of various starting materials ordinarily used in pharmaceutical preparations, non-pharmaceutical preparations, cosmetics etc.; for example, the starting base material includes animal and vegetable oils, mineral oil, ester oil, waxes, higher alcohols, fatty acids, silicon oil, surfactants, phospholipids, alcohols, polyvalent alcohols, water-soluble polymers, clay minerals, pure water etc., and if necessary, a pH adjuster, an antioxidant, a chelating agent, a preservative, a coloring agent, a perfume etc. can further be added. Further, ingredients having a differentiation-inducing action, a blood-stream promoting agent, a sterilizer, an antiinflammatory agent, a cell activator, vitamins, amino acids, a humectant and a keratin solubilizer can also be incorporated as necessary.

Although the dose of the acetylcholinesterase preparation according to the present invention is varied depending on severity of symptoms, age, sex, body weight, administration form, type of salt, chemical sensitivity and type of disease, and in the case of an adult, it is administered in a dose of generally about 30 μg to 1000 mg, preferably 100 μg to 500 mg and more preferably 100 μg to 100 mg for oral administration, or about 1 to 3000 μg/kg, preferably 3 to 10000 μg/kg for injection per day in one or several portions.

The acetylcholinesterase inhibitor according to the present invention exhibits an excellent inhibitory effect on acetylcholinesterase, and is useful as an agent for treating, preventing or improving senile dementia, cerebrovascular dementia or attention deficit hyperactivity disorder. In particular, it is useful as an agent for treating, preventing or improving Alzheimer type senile dementia.

EXAMPLES

Among the specific examples of the compounds as the active ingredient in the acetylcholinesterase inhibitor according to the present invention, the best mode is described below. The following examples and test example are described merely for illustrative purposes, and the compounds according to the present invention is not limited by the following specific examples in any case. The present invention can be carried out to the maximum by those skilled in the art by various modifications not only to the following examples but also to claims in the specification, and such modifications fall under patent claims of the specification.

Example 1

1-Benzyl-4-[(5.6-dimethoxy-1-indanone)-2-yl]methylpyridinium bromide

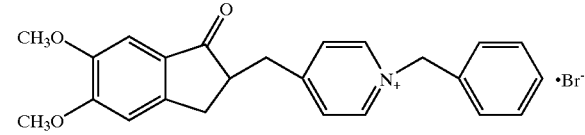

30 ml acetonitrile was added to 1.00 g (3.53 mmol) of 5,6-dimethoxy-2-(4-pyridyl)methyl-1-indanone, and the mixture was dissolved by heating under reflux. Then, 0.50 ml (4.21 mmol) benzyl bromide was added thereto. After heating under reflux for further 2.5 hours, it was left for cooling to room temperature and evaporated. 50 ml n-hexane was added to the residue. The precipitated crystals were separated by filtration and dried, to give 1.60 g of the title compound as pale yellow crystals (yield: quantitative). Melting point: 173–177° C. $^1$H-NMR (400 MHz, DMSO-$d_6$) δ (ppm) 2.70(1H, dd, J=3.6 Hz, J=16.4Hz), 3.01 (1H, dd, J=9.2 Hz, J=14 Hz), 3.12 (1H, dd, J=7.6 Hz, J=16.4 Hz), 3.16–3.24 (1H, m), 3.30–3.98 (1H, m), 3.77 (3H, s), 3.83 (3H, s), 5.81 (2H, s), 7.06 (1H, s), 7.07 (1H, s), 7.38–7.48 (3H, m), 7.50–7.56 (2H, m), 8.13 (2H, d, J=6.4 Hz), 9.14 (2H, d, J=6.4 Hz). ESI–MS: m/z=374 (M−Br)+.

Example 2

1-Benzyl-4-[(5,6-dimethoxy-1-indanone)-2-yl]methylpyridinium chloride

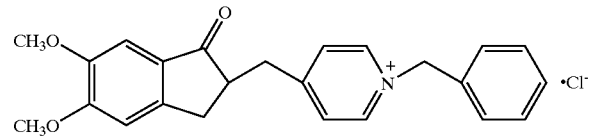

Example 3

1-Benzyl-4-[(1-indanone)-2-yl]methylpyridinium bromide

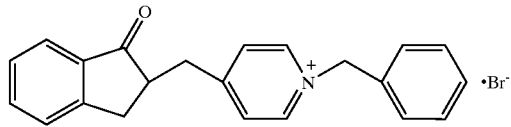

Example 4

1-Benzyl-4-[(5-methoxy-1-indanone)-2-yl]methylpyridinium bromide

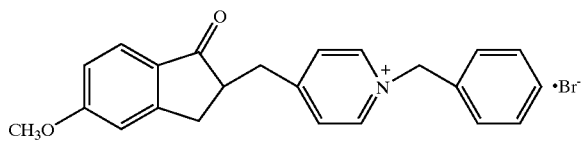

Example 5

1-Benzyl-4-[2-[(5,6-dimethoxy-1-indanone)-2-yl]ethyl]pyridinium bromide

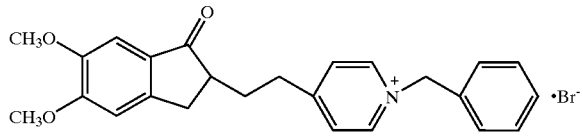

Example 6

1-Benzyl-4-[3-[(5,6-dimethoxy-1-indanone)-2-yl]propyl]pyridinium bromide

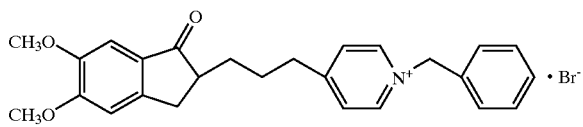

Example 7

1-Benzyl-4-[(5,6-dimethoxy-1-indanone)-2-ylidene]methylpyridinium bromide

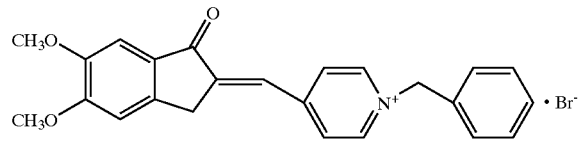

Example 8

1-(3-Fluorobenzyl)-4-[(5,6-dimethoxy-1-indanone)-2-yl]methylpyridinium bromide

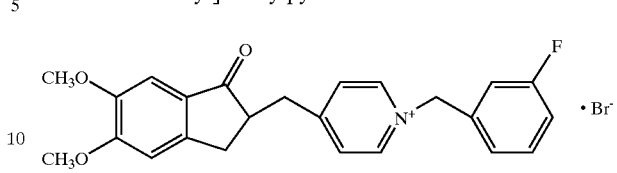

Example 9

1-(3-Methylbenzyl)-4-[(5,6-dimethoxy-1-indanone)-2-yl]methylpyridinium bromide

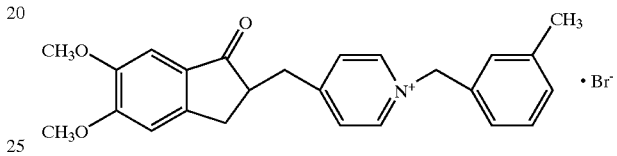

Example 10

1-(4-Hydroxybenzyl)-4-[(5,6-dimethoxy-1-indanone)-2-yl]methylpyridinium bromide

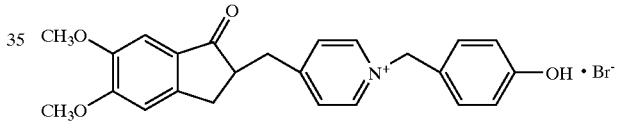

Example 11

1-Benzyl-4-[(5,6-dimethoxy-2-fluoro-1-indanone)-2-yl]methylpyridinium bromide

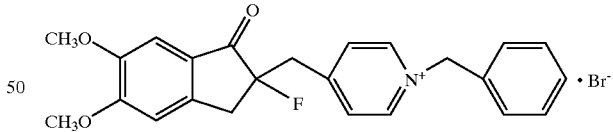

Example 12

1-(4-Hydroxybenzyl)-4-[(5,6-dimethoxy-2-fluoro-1-indanone)-2-yl]methylpyridinium bromide

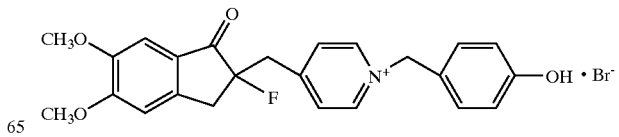

Test Example

Hereinafter, a pharmacological test example is shown to illustrate the usefulness of the compound according to the present invention as a medicament.

Inhibitory Effect on Acetylcholinesterase In Vitro

1) Test Method

Using a rat brain homogenate as a source of acetylcholinesterase, the esterase activity was determined in accordance with the method of Ellman et al[1]. Acetylthiocholine (as a substrate), a test compound and DTNB (5,5'-dithiobis(2-nitrobenzoic acid)) were added to the rat brain homogenate, and incubated. Then, the resulting yellow product produced by the reaction of the resulting thiocholine with DTNB was determined for the change in absorbance at 412 nm, to determine the acethylcholinesterase activity.

The inhibitory effect of each test compound on acetylcholinesterase was determined in terms of 50% inhibitory concentration ($IC_{50}$)

Each of the compounds was used after dissolved in physiological saline.

[1]; Ellman. G. L., Courtney, K. D., Andres, V. and Featherstone, R. M., (1961), Biochem. Pharmacol., 7, 88–95.

The pharmaceutical compositions comprising the title compounds of the above-mentioned Examples 1 to 12 exhibited an excellent acetylcholinesterase inhibitory effect. For example, the test result where the title compound of Example 1 was used is as follows:

TABLE 1

| Test Compound | $IC_{50}$ (nM) |
|---|---|
| Example 1 | 3.8 |
| Donepezil hydrochloride | 6.7 |

What is claimed is:

1. An acetylcholinesterase inhibitor comprising a 1-benzylpyridinium salt represented by the formula:

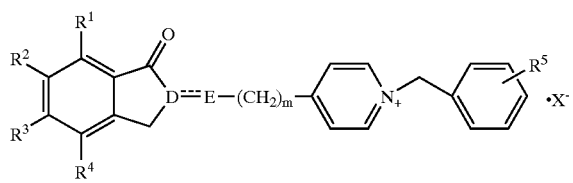

(I)

wherein $R^1$, $R^2$, $R^3$ and $R^4$ are the same as or different from each other and each represents a hydrogen atom, a halogen atom, a hydroxyl group, a nitrile group, a $C_{1-6}$ alkyl group, a $C_{1-6}$ alkoxy group, a $C_{1-6}$ alkoxycarbonyl group, a $C_{1-6}$ alkylaminocarbonyloxy group or a di($C_{1-6}$ alkyl)-aminocarbonyloxy group; $R^5$ represents a hydrogen atom, a halogen atom, a $C_{1-6}$ alkyl group, a $C_{2-6}$ alkenyl group or a $C_{2-6}$ alkynyl group; the partial structure:

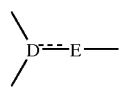

means a group represented by the formula >C($R^6$)—CH$_2$— (wherein $R^6$ is a hydrogen atom or a halogen atom) or >C=CH—; $X^-$ represents an organic sulfonic acid ion selected from the group consisting of methanesulfonate ion, trifluoromethanesulfonate ion, ethanesulfonate ion, benzenesulfonate ion, toluenesulfonate ion and camphorsulfonate ion; and m is 0 or an integer from 1 to 5.

2. A method of inhibiting acetylcholinesterase in a mammal in need thereof comprising administering a pharmaceutically effective amount of a 1-benzylpyridinium salt represented by the formula:

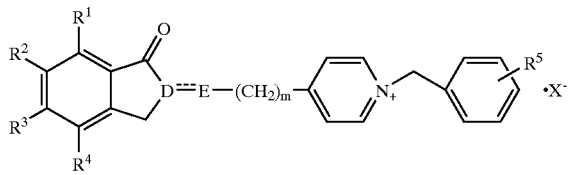

(I)

wherein $R^1$, $R^2$, $R^3$ and $R^4$ are the same as or different from each other and each represents a hydrogen atom, a halogen atom, a hydroxyl group, a nitrile group, a $C_{1-6}$ alkyl group, a $C_{1-6}$ alkoxy group, a $C_{1-6}$ alkoxycarbonyl group, a $C_{1-6}$ alkylaminocarbonyloxy group or a di($C_{1-6}$ alkyl)-aminocarbonyloxy group; $R^5$ represents a hydrogen atom, a halogen atom, a $C_{1-6}$ alkyl group, a $C_{2-6}$ alkenyl group or a $C_{2-6}$ alkynyl group; the partial structure:

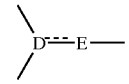

means a group represented by the formula >C($R^6$)—CH$_2$— (wherein $R^6$ is a hydrogen atom or a halogen atom) or >C=CH—; $X^{31}$ represents a halide ion or organic sulfonic acid ion; m is 0 or an integer from 1 to 5.

3. A method of preventing, treating or improving a disease against which an inhibitory action on acetylcholinesterase is efficacious for prevention, treatment or improvement, by administering to a patient a pharmacologically effective dose of the 1-benzylpyridinium salt represented by the formula (I)

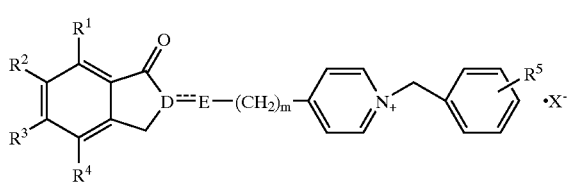

(I)

wherein $R^1$, $R^2$, $R^3$ and $R^4$ are the same as or different from each other and each represents a hydrogen atom, a halogen atom, a hydroxyl group, a nitrile group, a $C_{1-6}$ alkyl group, a $C_{1-6}$ alkoxy group, a $C_{1-6}$ alkoxycarbonyl group, a $C_{1-6}$ alkylaminocarbonyloxy group or a di($C_{1-6}$ alkyl)-aminocarbonyloxy group; $R^5$ represents a hydrogen atom, a halogen atom, a $C_{1-6}$ alkyl group, a $C_{2-6}$ alkenyl group or a $C_{2-6}$ alkynyl group; the partial structure:

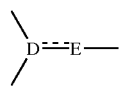

means a group represented by the formula >C($R^6$)—$CH_2$— (wherein $R^6$ is a hydrogen atom or a halogen atom) or >C=CH—; $X^{31}$ represents a halide ion or organic sulfonic acid ion; m is 0 or an integer from 1 to 5.

4. The method according to claim 2, wherein $X^-$ is a chloride ion or bromide ion.

5. The method according to claim 3, wherein chloride ion or bromide ion.

6. The method of claim 2 wherein $R^1$, $R^2$, $R^3$ and $R^4$ are the same as or different from each other and each represents a hydrogen atom or a $C_{1-6}$ alkoxy group.

7. The method of claim 2 wherein $R^1$, $R^2$, $R^3$ and $R^4$ are the same as or different from each other and each represents a hydrogen atom or a methoxy group.

8. The method of claim 2 wherein $R^1$ and $R^4$ represent a hydrogen atom; and $R^2$ and $R^3$ represent a methoxy group.

9. The method of claim 2 wherein $R^5$ is a hydrogen atom.

10. The method of claim 2 wherein the partial structure:

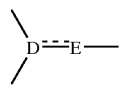

is a group represented by the formula >C($R^6$)—$CH_2$— (wherein $R^6$ represents a hydrogen atom or a halogen atom).

11. The method of claim 2 wherein m is 0, 2 or 4.

12. The method of claim 2 wherein the halide ion represented by $X^{31}$ is a chloride ion, bromide ion or iodide ion.

13. The method of claim 2 wherein the organic sulfonic acid ion represented by $X^-$ is methanesulfonate ion, trifluoromethanesulfonate ion, ethanesulfonate ion, benzenesulfonate ion, toluenesulfonate ion and camphorsulfonate ion.

14. The method of claim 2 wherein the 1-benzylpyridinium salt is a compound represented by the formula:

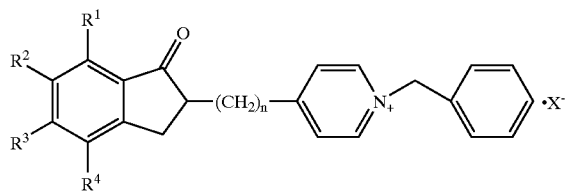

wherein $R^1$, $R^2$, $R^3$, $R^4$ and $X^{31}$ have the same meanings as defined above; and n is an integer from 1 to 6.

15. The method of claim 2 wherein the 1-benzylpyridinium salt is a compound represented by the formula:

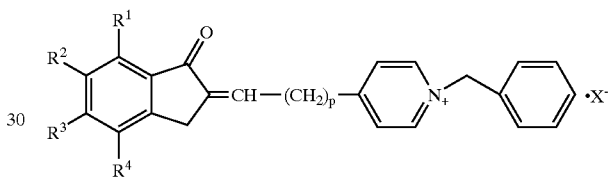

wherein $R^1$, $R^2$, $R^3$, $R^4$ and $X^{31}$ have the same meanings as defined above; and p is an integer from 0 to 5.

* * * * *

UNITED STATES PATENT AND TRADEMARK OFFICE
CERTIFICATE OF CORRECTION

PATENT NO. : 6,706,741 B2
DATED : March 16, 2004
INVENTOR(S) : Iimura et al.

It is certified that error appears in the above-identified patent and that said Letters Patent is hereby corrected as shown below:

Title page,
Item [54], please correct the title to read as follows:
-- ACETYLOCHOLINESTERASE INHIBITOR COMPRISING 1-BENZYLPYRIDINIUM SALT --

Column 14,
Line 41, change "$X^{31}$" to -- $X^-$ --.

Column 15,
Lines 11 and 38, change "$X^{31}$" to -- $X^-$ --.
Line 15, after "wherein", insert -- $X^-$ is a --.

Column 16,
Lines 20 and 34, change "$X^{31}$" to -- $X^-$ --.

Signed and Sealed this

Thirty-first Day of August, 2004

JON W. DUDAS
*Director of the United States Patent and Trademark Office*